(12) United States Patent
Buettgen et al.

(10) Patent No.: US 10,466,355 B2
(45) Date of Patent: Nov. 5, 2019

(54) OPTOELECTRONIC MODULES FOR DISTANCE MEASUREMENTS AND SUPPLEMENTAL MEASUREMENTS

(71) Applicant: AMS SENSORS SINGAPORE PTE. LTD., Singapore (SG)

(72) Inventors: Bernhard Buettgen, Adliswil (CH); Jens Geiger, Thalwil (CH); Michael Kiy, Winterthur (CH); Oliver Chidley, Regensdorf (CH); Markus Rossi, Jona (CH)

(73) Assignee: AMS SENSORS SINGAPORE PTE. LTD., Singapore (SG)

(*) Notice: Subject to any disclaimer, the term of this patent is extended or adjusted under 35 U.S.C. 154(b) by 0 days.

(21) Appl. No.: 15/687,884

(22) Filed: Aug. 28, 2017

(65) Prior Publication Data

US 2018/0059246 A1    Mar. 1, 2018

Related U.S. Application Data

(60) Provisional application No. 62/380,576, filed on Aug. 29, 2016.

(51) Int. Cl.
| | |
|---|---|
| *G01S 17/36* | (2006.01) |
| *G01S 7/481* | (2006.01) |
| *G06F 3/01* | (2006.01) |
| *G01S 7/497* | (2006.01) |
| *A61B 5/024* | (2006.01) |
| *G01S 17/89* | (2006.01) |
| *A61B 5/1455* | (2006.01) |
| *G06F 3/03* | (2006.01) |

(52) U.S. Cl.
CPC .............. *G01S 17/36* (2013.01); *A61B 5/024* (2013.01); *A61B 5/02416* (2013.01); *A61B 5/14551* (2013.01); *G01S 7/4813* (2013.01); *G01S 7/497* (2013.01); *G01S 17/89* (2013.01); *G06F 3/017* (2013.01); *G06F 3/0304* (2013.01)

(58) Field of Classification Search
None
See application file for complete search history.

(56) References Cited

U.S. PATENT DOCUMENTS

| | | | | |
|---|---|---|---|---|
| 5,088,817 A | * | 2/1992 | Igaki .................. | G06K 9/00046 250/556 |
| 5,800,348 A | * | 9/1998 | Kaestle .............. | G01N 21/3151 600/322 |
| 6,906,793 B2 | * | 6/2005 | Bamji ..................... | G01C 3/00 348/302 |

(Continued)

FOREIGN PATENT DOCUMENTS

WO    WO 2015/136100    9/2015

*Primary Examiner* — Lex H Malsawma
(74) *Attorney, Agent, or Firm* — Michael Best & Friedrich LLP

(57) ABSTRACT

An optoelectronic module includes a first light emitter operable to emit radiation at a first wavelength toward an object outside the module. The module also includes demodulation pixels operable to detect radiation of the first wavelength reflected from the object. One or more processors are operable to determine a distance to the object based on the radiation detected by the demodulation pixels. The module is further operable to perform a supplemental measurement other than distance.

17 Claims, 5 Drawing Sheets

(56) References Cited

U.S. PATENT DOCUMENTS

| | | | |
|---|---|---|---|
| 2003/0044051 A1* | 3/2003 | Fujieda | G06K 9/00067 382/124 |
| 2009/0232367 A1* | 9/2009 | Shinzaki | G06K 9/0012 382/124 |
| 2010/0008552 A1* | 1/2010 | Shin | G06K 9/0012 382/124 |
| 2010/0026453 A1* | 2/2010 | Yamamoto | G06F 21/32 340/5.83 |
| 2011/0028814 A1* | 2/2011 | Petersen | A61B 5/14552 600/324 |
| 2011/0043806 A1* | 2/2011 | Guetta | G01S 17/026 356/432 |
| 2012/0033045 A1* | 2/2012 | Schweizer | G01S 7/4912 348/46 |
| 2015/0057511 A1* | 2/2015 | Basu | A61B 5/02433 600/323 |
| 2015/0230743 A1* | 8/2015 | Silveira | A61B 5/7221 600/323 |
| 2015/0340351 A1 | 11/2015 | Rossi et al. | |
| 2015/0374245 A1 | 12/2015 | Szilagyi | |
| 2016/0073954 A1 | 3/2016 | Meitav | |
| 2018/0059218 A1* | 3/2018 | Buettgen | G01S 7/483 |

\* cited by examiner

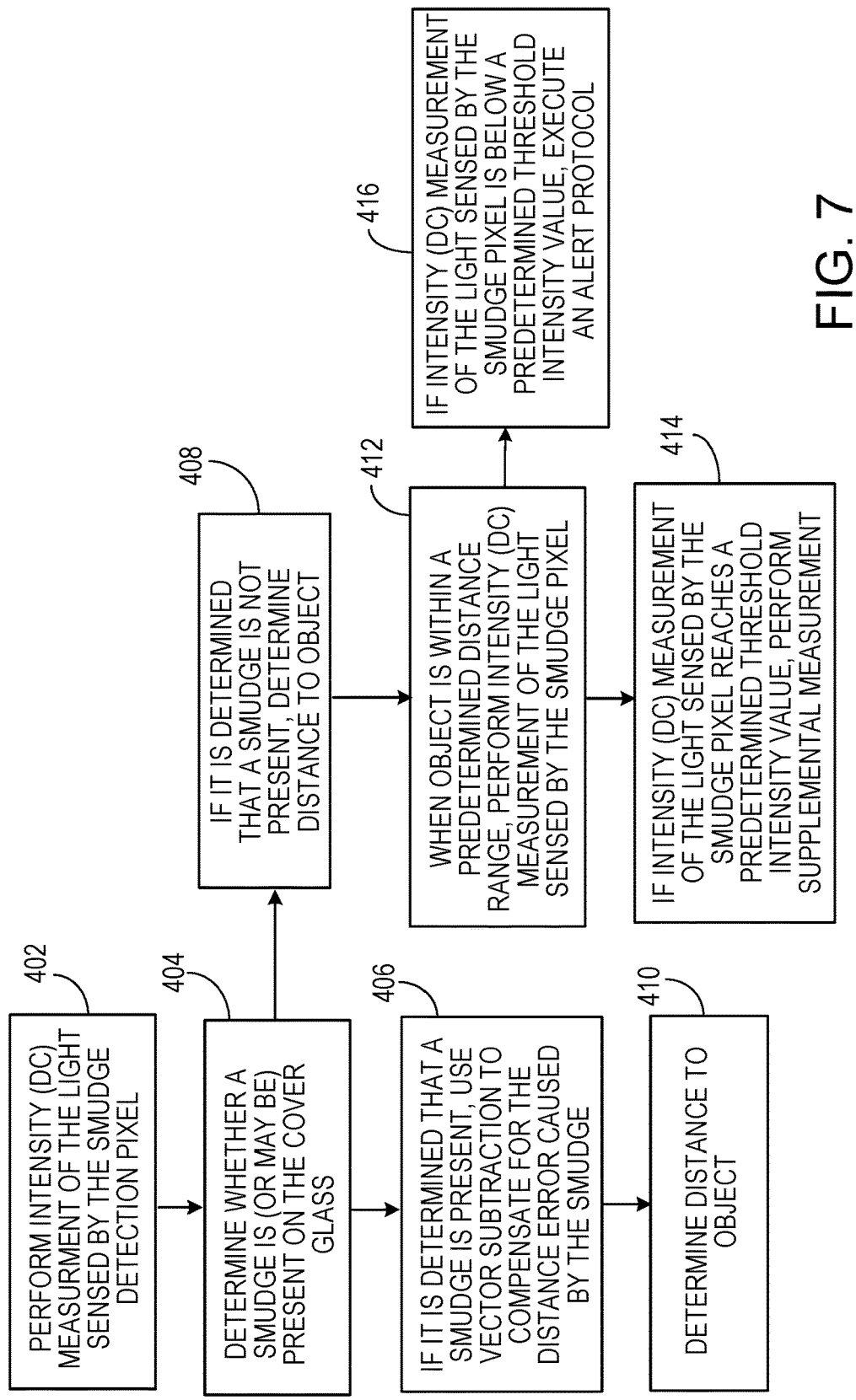

OPTOELECTRONIC MODULES FOR DISTANCE MEASUREMENTS AND SUPPLEMENTAL MEASUREMENTS

CROSS-REFERENCE TO RELATED APPLICATION(S)

The present application claims the benefit of priority of U.S. Provisional Application No. 62/380,576, filed on Aug. 29, 2016. The entire contents of the earlier application are incorporated herein by reference.

FIELD OF THE DISCLOSURE

This disclosure relates to optoelectronic modules and methods for distance measurements and supplemental measurements.

BACKGROUND

Some handheld computing devices such as smart phones can provide a variety of different optical functions such as one-dimensional (1D) or three-dimensional (3D) gesture detection, 3D imaging, time-of-flight or proximity detection, ambient light sensing, and/or front-facing two-dimensional (2D) camera imaging.

Time-of-flight (TOF) sensors, for example, can be used to detect the distance to an object. In general, TOF systems are based on the phase-measurement technique of emitted intensity-modulated light, which is reflected by a scene. The reflected light is imaged onto a sensor, and the photo-generated electrons are demodulated in the sensor. Based on the phase information, the distance to a point in the scene for each pixel is determined by processing circuitry associated with the sensor.

SUMMARY

This disclosure describes optoelectronic modules and methods for distance measurements and supplemental measurements.

In one aspect, for example, the disclosure describes an optoelectronic module including a first light emitter operable to emit radiation at a first wavelength toward an object outside the module. The module also includes demodulation pixels operable to detect radiation of the first wavelength reflected from the object. One or more processors are operable to determine a distance to the object based on the radiation detected by the demodulation pixels. The module is further operable to perform a supplemental measurement other than distance.

Some implementations include one or more of the following features. For example, in some implementations, the supplemental measurement is a heart rate measurement. In some implementations, the module includes a second light emitter operable to emit radiation at a second wavelength different from the first wavelength, and the module is operable to use the second light emitter to perform the supplemental measurement. In such cases, the supplemental measurement can be, for example, a blood oxygen measurement.

In another aspect, the disclosure describes a method of operating an optoelectronic module comprising demodulation pixels. The method includes emitting light from the module toward an object outside the module at a first modulation frequency and at a second modulation frequency, and detecting, in the demodulation pixels, light reflected from the object at the first modulation frequency and light reflected from the object at the second modulation frequency. The method includes subtracting out a component in signals detected by the demodulation pixels, wherein the component is caused by a reflection from an element in or on the optoelectronic module or host device in which the optoelectronic module is disposed, so as to determine a phase shift and amplitude resulting from light reflected by the object. The method further includes determining that the object is within a predetermined distance range by determining the distance to the object based at least in part on the phase shift resulting from light reflected by the object; executing an object signal-recognition protocol using the light detected in the demodulation pixels; and subsequently initiating execution of a supplemental measurement automatically in response to the object signal-recognition protocol determining that the object satisfies predetermined criteria.

In yet another aspect, the disclosure describes an apparatus that includes an optoelectronic module and one or more processors. The module includes a light emitter operable to emit light from the module toward an object outside the module at a first modulation frequency and at a second modulation frequency, and demodulation pixels operable to detect light reflected from the object at the first modulation frequency and at the second modulation frequency. The one or more processors are operable to subtract out a component in signals detected by the demodulation pixels, wherein the component is caused by a reflection from an element in or on the optoelectronic module or host device in which the optoelectronic module is disposed, so as to determine a phase shift and amplitude resulting from light reflected by the object. The one or more processors are further operable to determine that the object is within a predetermined distance range by determining the distance to the object based at least in part on the phase shift resulting from light reflected by the object, execute an object signal-recognition protocol using the light detected in the demodulation pixels, and subsequently initiate execution of a supplemental measurement in response to the object signal-recognition protocol determining that the object satisfies predetermined criteria.

Some implementations include one or more of the following features. For example, the object signal-recognition protocol can be executed using the distance to the object and/or the amplitude resulting from the light reflected by the object. In some instances, vector manipulation is used to subtract out the phase shift caused by the reflection from the element in the optoelectronic module or host device in which the optoelectronic module is disposed. The reflection can be, for example, from a smudge on a cover glass of the host device. In some instances, the supplemental measurement includes a measurement of pulse, heartrate, and/or blood oxygen level. In some implementations, the optoelectronic module itself is operable to execute the supplemental measurement.

In some implementations, a determination is made as to whether the amplitude resulting from the light reflected by the object is greater than or equal to a predetermined threshold intensity value. The supplemental measurement protocol can be executed upon determination that the amplitude resulting from the light reflected by the object is greater than or equal to the predetermined threshold intensity value. Likewise, in some cases, a determination is made as to whether the amplitude resulting from the light reflected by the object is less than a predetermined threshold intensity value. An alert protocol can be executed upon determination that the amplitude resulting from light reflected by the object is less than the predetermined threshold intensity value.

In some instances, execution of the supplemental measurement is triggered in response to the object signal-recognition protocol recognizing a gesture as an actual or virtual click or multi-click of a cover glass of a host device in which the module is disposed.

Other aspects, features and various advantages will be readily apparent from the following detailed description, the accompanying drawings, and the claims.

BRIEF DESCRIPTION OF THE DRAWINGS

FIG. 7 illustrates an example of a method that includes performing an alert protocol.

DETAILED DESCRIPTION

Figure 1:
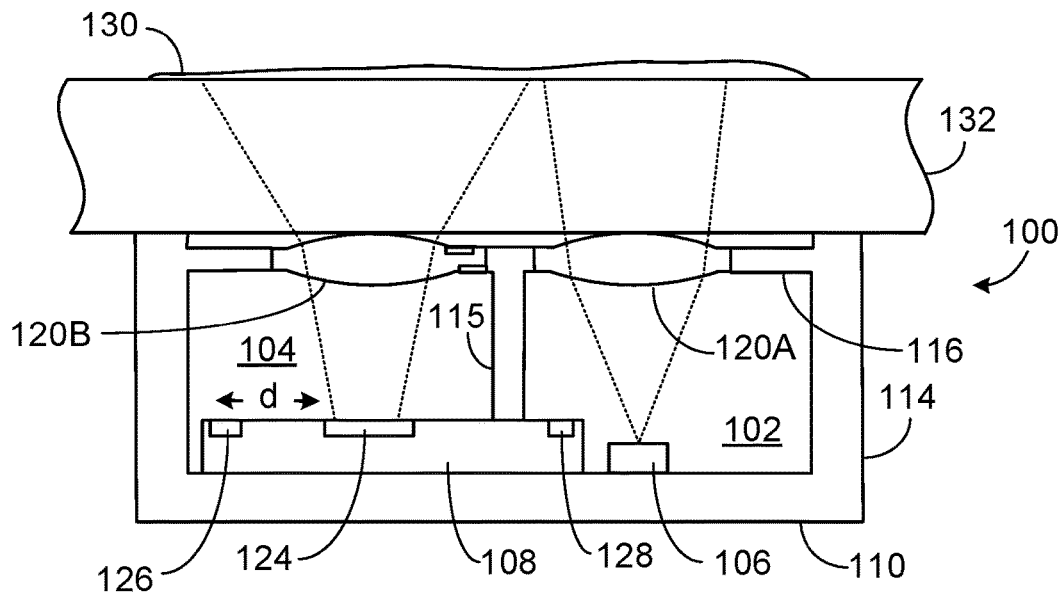
FIG. 1 illustrates an example of an optoelectronic module.

FIG. 1 illustrates an example of an optoelectronic module 100 that includes a light emission channel 102 and a light detection channel 104. A light emitter 106 (i.e., an illumination source) and a TOF sensor 108 are mounted on a first side of a printed circuit board (PCB) 110, which forms the bottom side of the module housing. The light emitter 106 can be operable to generate coherent, directional, spectrally defined light emission with minimal divergence relative to the emission axis (e.g., in the range of 10 to 20 degrees). Examples of the light emitter 106 are a laser diode or a vertical cavity surface emitting laser (VCSEL).

A spacer 114 is attached to the first side of the PCB 110 and separates the PCB 110 from an optics member 116. The spacer 114 can be composed of a material (e.g., epoxy resin) and have a thickness such that it is substantially non-transparent to wavelengths of light detectable by the TOF sensor 108. An interior wall 115 of the spacer 114 provides optical isolation between the module's two chambers (i.e., the light emission chamber (channel) 102 and the light detection chamber (channel) 104).

The optics member 116 includes a respective passive optical element (e.g., a lens) 120A, 120B for each channel 102, 104. Light from the emitter 106 is directed out of the module 100 and, if reflected by an object back toward the module's detection channel 104, can be sensed by the TOF sensor 108.

The TOF sensor 108 includes an array of spatially distributed light sensitive elements (e.g., pixels), as well as logic and other electronics to read and process the pixel signals. The pixels can be implemented, for example, in a single integrated semiconductor chip (e.g., a CCD or CMOS sensor). The emitter 106 and the TOF sensor 108 can be connected electrically to the PCB 110, for example, by conductive pads or wire bonds. The PCB 110, in turn, can be connected electrically to other components within a host device (e.g., a smart phone). The TOF sensor 108 is operable to resolve distance based on the known speed of light by measuring the time-of-flight of a light signal between the sensor and the subject for each point of an object. The circuitry in the TOF sensor 108 can use signals from the pixels to calculate, for example, the time the light has taken to travel from the emitter to an object of interest and back to the focal plane array.

The TOF sensor 108 can be implemented, for example, as an integrated sensor chip. As shown in FIG. 1, the TOF sensor 108 includes active demodulation detection pixels 124, one or more dedicated "spurious reflection detection" pixels 126 and one or more reference pixels 128. Although the number and arrangement of the demodulation detection pixels 124 can vary depending on the implementation, in some implementations, the demodulation detection pixels are in a 3×3 array. In some cases, the spurious-reflection detection pixels may be referred to as smudge detection pixels. Each spurious-reflection detection pixel 126 can be implemented, for example, as a CCD pixel or a photodiode. The demodulation detection pixels 124 provide the primary signals for determining the proximity of an object outside the module. The demodulation detection pixels 124 preferably are centered below the light detection channel lens 120B. The center optical emission axis of the emitter 106 preferably is aligned with the emitter channel lens 120A. Signals sensed by the spurious-reflection detection pixel(s) 126 can be used to correct for spurious reflections such as from a smudge (i.e., a blurred or smeared mark such as a fingerprint or dirt) 130 on the transmissive cover (e.g., a cover glass) 132 of a host device (e.g., a smart phone or other handheld computing device). In some implementations, signals sensed by the spurious-reflection detection pixel(s) 126 can be used to correct for spurious reflections resulting from other direct reflections such as from the cover glass, from a filter, or from other optical/non-optical components in the optoelectronic module or host device. If such corrections are not performed, the TOF sensor may produce a spurious output signal, which can compromise the accuracy of the proximity data collected. A small amount of light from the emitter 106 can be reflected, for example, by the lens 120A back toward the reference pixel(s) 128. Signals from the reference pixel(s) 128 can be used to compensate for thermal drift and/or to provide a zero distance measurement.

The sensor's processing circuitry can be implemented, for example, as one or more integrated circuits in one or more semiconductor chips with appropriate digital logic and/or other hardware components (e.g., read-out registers; amplifiers; analog-to-digital converters; clock drivers; timing logic; signal processing circuitry; and/or a microprocessor). The processing circuitry may reside in the same semiconductor chip as the sensor 108 or in one or more other semiconductor chips.

In the example of FIG. 1, an interior wall 115 of the spacer 114 provides optical isolation between the module's two chambers (i.e., the light emission channel 102 and the light detection channel 104). The reference pixel(s) 128 are located in the emitter chamber 102, whereas the demodulation detection pixels 124 and the dedicated spurious-reflection detection pixel(s) 126 are located in the detection chamber 104. The interior wall 115 prevents emitter light, which is reflected, for example, back into the emission chamber 102 by the lens 120A, from impinging on the demodulation detection pixels 124.

In some of the examples described here, it is assumed that spurious reflections may be caused by a smudge on the cover glass of the host device. However, the modules and techniques described below also can be applicable to spurious reflections resulting from other direct reflections such as from the cover glass, from a filter, or from other optical/non-optical components in the optoelectronic module or host device.

In some cases, the spurious-reflection detection pixel(s) 126 is positioned relative to the demodulation detection pixels 124 such that, in the absence of a smudge on cover 132 of the host device, the spurious-reflection detection pixel 126 senses, at most, a signal representing only a relatively low optical intensity of light reflected by an object in a scene outside the module 100. In contrast, when a smudge 130 is present on the surface of the cover 132 of the host device, the smudge may redirect some of the light reflected by the external object toward the spurious-reflection detection pixel(s) 126 such that they sense a significantly higher optical intensity. For example, the spurious-reflection detection pixel 126 can be positioned on the sensor 108 a sufficient lateral distance (d) from the demodulation detection pixels 124 such that, in the absence of a smudge on cover 132 of the host device, the spurious-reflection detection pixel 126 senses, at most, only a relatively low optical intensity of light reflected by an object in a scene outside the module 100. On the other hand, a smudge 130 on the surface of the cover 132 of the host device can cause some of the light reflected by the external object to be redirected toward the spurious-reflection detection pixel 126 such that it senses a significantly higher optical intensity.

Figure 2:
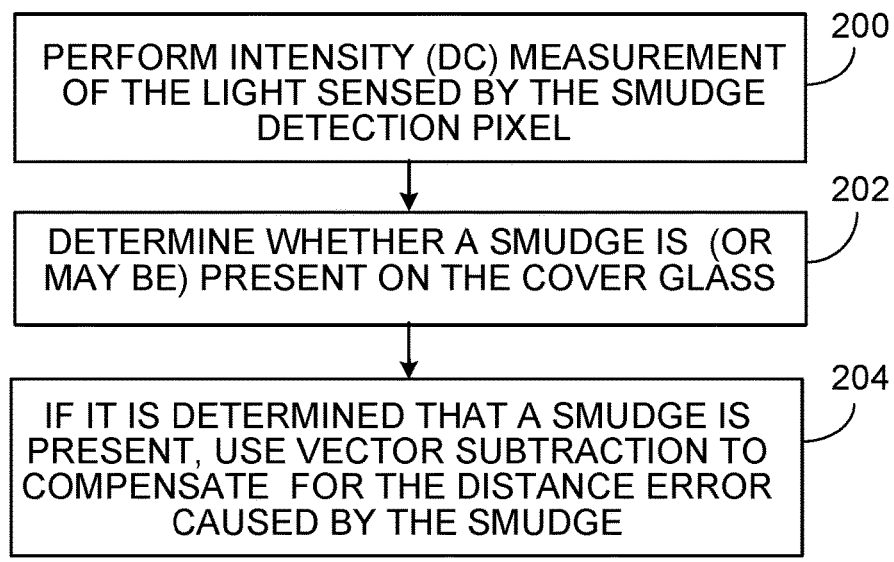
FIG. 2 is a flow chart illustrating a method of compensating for spurious reflections.

The optical intensity sensed by the spurious-reflection detection pixel 126 can be used by the sensor's processing circuitry to determine whether a smudge is present on the cover glass 132 and to determine how much light (i.e., amplitude and phase) collected by the active pixels 124 results from the smudge rather than the object of interest. For example, as illustrated by FIG. 2, during each TOF frame, the sensor's control circuitry can initiate an intensity (DC) measurement of the light sensed by the spurious-reflection detection pixel 126 (block 200). Based at least in part on the output of the spurious-reflection detection pixel, the sensor's processing circuitry then can determine whether a smudge is present on the cover glass 132 (block 202). In particular, in some implementations, a high intensity sensed by the spurious-reflection detection pixel 126 in combination with a TOF sensor output of about zero (i.e., cover glass level) indicates the presence of an object on the surface of the cover glass 132. On the other hand, a high intensity sensed by the spurious-reflection detection pixel 126 in combination with a TOF measurement greater than zero indicates the presence of a smudge. Further, the intensity sensed by the spurious-reflection detection pixel 126 is proportional to the magnitude of the smudge vector. As the phase of the smudge vector is available to the sensor's processing circuitry, the processing circuitry can use vector subtraction to compensate for the distance error caused by the smudge (block 204). For example, the intensity of the light reflected by the smudge 130 can be measured by the spurious reflection pixel 126. Assuming that the path length to the smudge 130 is known to the sensor's processing circuitry, the phase also can be determined (e.g., as part of a calibration process). If the magnitude of the light on the spurious-reflection detection pixel 126 is known, the magnitude of the light component incident on the active pixels 124 that is a result of reflection from the smudge 130 can be inferred, e.g., by the sensor's processing circuitry. The phase of the light component that is a result of the reflection from the smudge 130 can be factored out of the measured signals obtained from the active pixels 124.

Figure 3:
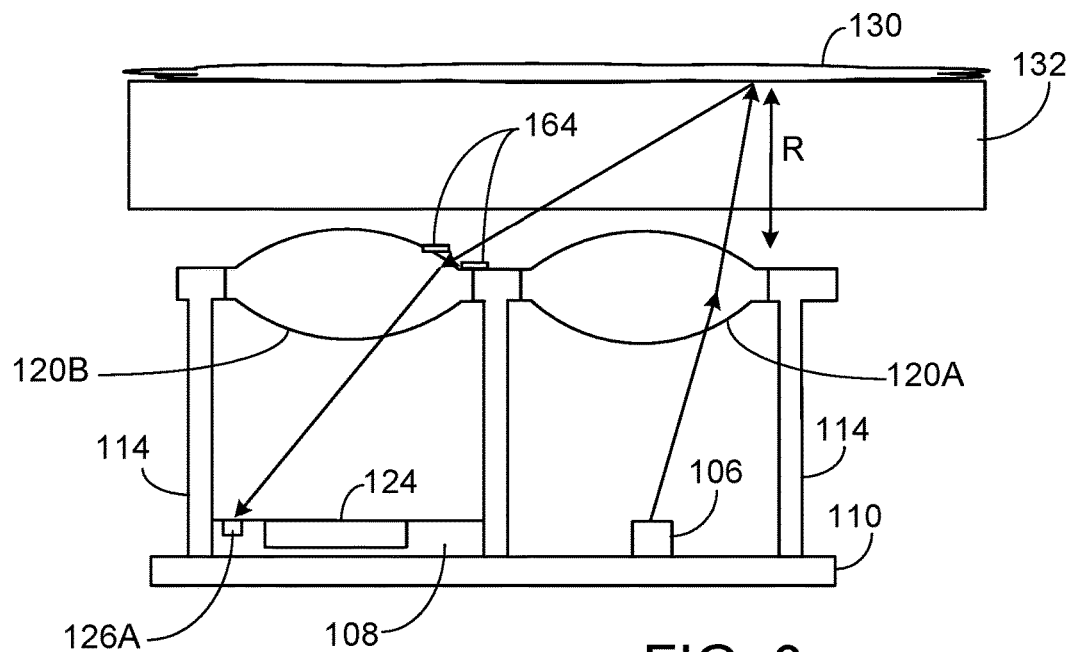
FIG. 3 illustrates a further example of an optoelectronic module.

In some implementations, the module includes pixels that serve as combined reference and spurious-reflection detection pixels. An example is illustrated in FIG. 3, which includes one or more pixels 126A whose output can be used by the sensor's processing circuitry to correct for spurious reflections such as from a smudge and also to compensate for thermal drift/or and to provide a zero distance measurement. For example, signals from the pixels 126A can be used to determine both amplitude and phase during calibration of the module. During subsequent operation, changes in amplitude of the detected signals of the pixels 126A can indicate the presence of the smudge and can be used to correct for spurious reflections caused by the smudge. Likewise, phase shifts in the detected signals of the pixels 126A can be used to compensate for thermal drift.

In some implementations, instead of, or in addition to, dedicated spurious-reflection detection (i.e., smudge) pixels, signals obtained from the demodulation detection pixels 124 can be used to determine the wave component (i.e., amplitude, phase) that is caused by reflection from a smudge 130 on the surface of the cover glass 132. To do so, the wave component caused by the smudge reflection can be estimated, for example, by repeating measurements at two different modulation frequencies. Assuming the distance between the smudge 130 and the emitter 106 is known to the module's processing circuitry (e.g., based on a previously stored value in memory and/or calibration of the module), the additional wave component resulting from the presence of the smudge 130 can be determined by the processing circuitry. Any such additional wave component would be common to signals detected by the demodulation detection pixels 124 at both modulation frequencies. The additional wave component caused by the smudge 130 can be eliminated (i.e., subtracted out) through known vector manipulation techniques, and the wave components resulting from light reflected by the object of interest outside the module can be calculated. The resulting phase shift then can be used to calculate the distance to the object 135.

Figure 4:
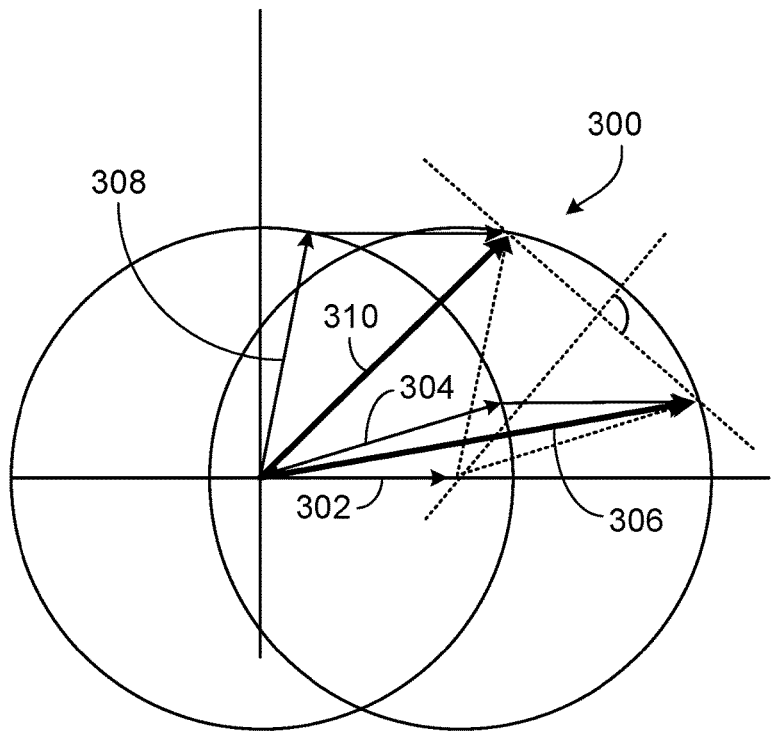
FIG. 4 is an example of a phasor diagram based on measurements using two different modulation frequencies.

FIG. 4 is an example of a phasor diagram 300 illustrating the various light components in which two different modulation frequencies are used as described above. In FIG. 4, 302 is the wave component (i.e., vector representing amplitude, phase) caused by reflection from the smudge, 304 is the wave component caused by light reflected from the object at the low modulation frequency, 306 is the wave component that represents the sum of the light reflected both by the object and by the smudge at the low modulation frequency, 308 is the wave component caused by light reflected from the object at the high modulation frequency, and 310 is the wave component that represents the sum of the light reflected both by the object and by the smudge at the high modulation frequency. The wave components (i.e., phasors) 302, 304, 306, 308 and 310 in FIG. 4 are rotated by a phase corresponding to the known distance of the smudge measured at the respective modulation frequency. In the phasor diagram 300, the two phasors 306, 310 (representing the received light signal at low and high demodulation frequencies, respectively) lie on a circle whose center corresponds to the amplitude of the smudge component. Thus, vector manipulation can be used to eliminate the wave component caused by the smudge. The foregoing vector manipulation to eliminate the wave component caused by the smudge can be performed by the sensor's processing circuitry or by control circuitry of a host device in which the module is disposed.

The modules and techniques described above can be used, for example, to facilitate more accurate determinations of whether an object is within a predetermined distance range by determining the distance to the object based, at least in part, on the phase shift resulting from light reflected by the object. An object signal-recognition protocol then can be executed, for example, based on the determined distance to the object and/or the intensity (or amplitude) of light reflected by the object and incident on the active pixels 124 and/or the spurious-reflection detection pixel 126. Known object signal-recognition protocols can be used to identify an object based on the data acquired from the demodulation pixels. Further, in some instances, the results of the object signal-recognition protocol can trigger execution of a corresponding supplemental measurement (e.g., measurement of a person's pulse, heartrate and/or blood oxygen level using, for example, a pulse oximeter, a heartrate monitor or other biometric sensor in the TOF module 100 or in the host device that is based at least in part on optical techniques).

In some instances, the TOF module itself can be used to perform the supplemental measurement. For example, if the light source 106 is operable to emit infra-red ("IR") radiation (e.g., 940 nm), the light source can be used for pulse or heart rate measurements as well as the distance measurement. In some cases, the TOF module includes one or more additional light sources, and/or optical filters on some or all of the pixels, so that the module is able to perform the supplemental measurement. For example, a second light source (e.g., operable to emit red light, for example, at 660 nm) can be included in the module to facilitate blood oxygen measurements based on $HbO_2$ absorption. Also, if the main demodulation pixels 124 have an IR pass filter, they cannot detect radiation emitted by the second light source at 660 nm. Therefore, in such implementations, the module can include one or more dedicated pixel(s) to detect the second light source, or the smudge pixels 126 can be used to detect the second wavelength.

In some cases, control circuitry in the host device or in the module 100 itself is operable to determine whether light reflected by the object is less than a predetermined threshold intensity value. The control circuitry (which can be coupled to receive output from the optoelectronic module's sensor) is further operable to execute an alert protocol if it is determined that the amplitude resulting from light reflected by the object is less than the predetermined threshold intensity value. In other cases, the control circuitry is operable to execute an alert protocol if it is determined that the amplitude resulting from light reflected by the object is equal to or greater than the predetermined threshold intensity value. The following paragraphs describe specific applications of the foregoing features.

For example, in some implementations, the object whose distance is to be detected is a finger (or fingers) of a person using a host device that includes a cover glass protecting an optoelectronic module 100 disposed within the device. In such situations, the object signal-recognition protocol can identify a predetermined gesture such as an actual or virtual click, which may include rapidly moving the finger once toward and away from the optoelectronic module 100. An actual click includes the user lightly touching (e.g., with her finger) the cover glass of the host device in which the optoelectronic model 100 is disposed, whereas a virtual click involves the user moving the finger toward and away the module without touching the cover glass. In another example, an actual or virtual double-click may include rapidly moving the finger twice toward and away from the optoelectronic module 100. In both examples, once the object signal-recognition protocol is associated with a pre-determined gesture, the protocol can be used to initiate execution of a corresponding supplemental measurement automatically in response to detecting the particular gesture. For example, an actual or virtual (single) click would initiate execution of a supplemental measurement by the module or the host device to measure the person's pulse rate, whereas an actual or virtual double-click would initiate execution of a supplemental measurement by the module or the host device to measure the person's blood oxygen levels. In other implementations, an actual or virtual (single) click would initiate execution of a supplemental measurement to measure blood oxygen levels, whereas an actual or virtual double click would initiate execution of a supplemental measurement to measure pulse rate. In yet other implementations, the clicks would initiate other types of measurements. Further, in addition to single and double clicks, some implementations may include other multi-clicks (e.g., three or more actual or virtual clicks) that initiate a corresponding pre-specified supplemental measurement by the device.

Figure 5:
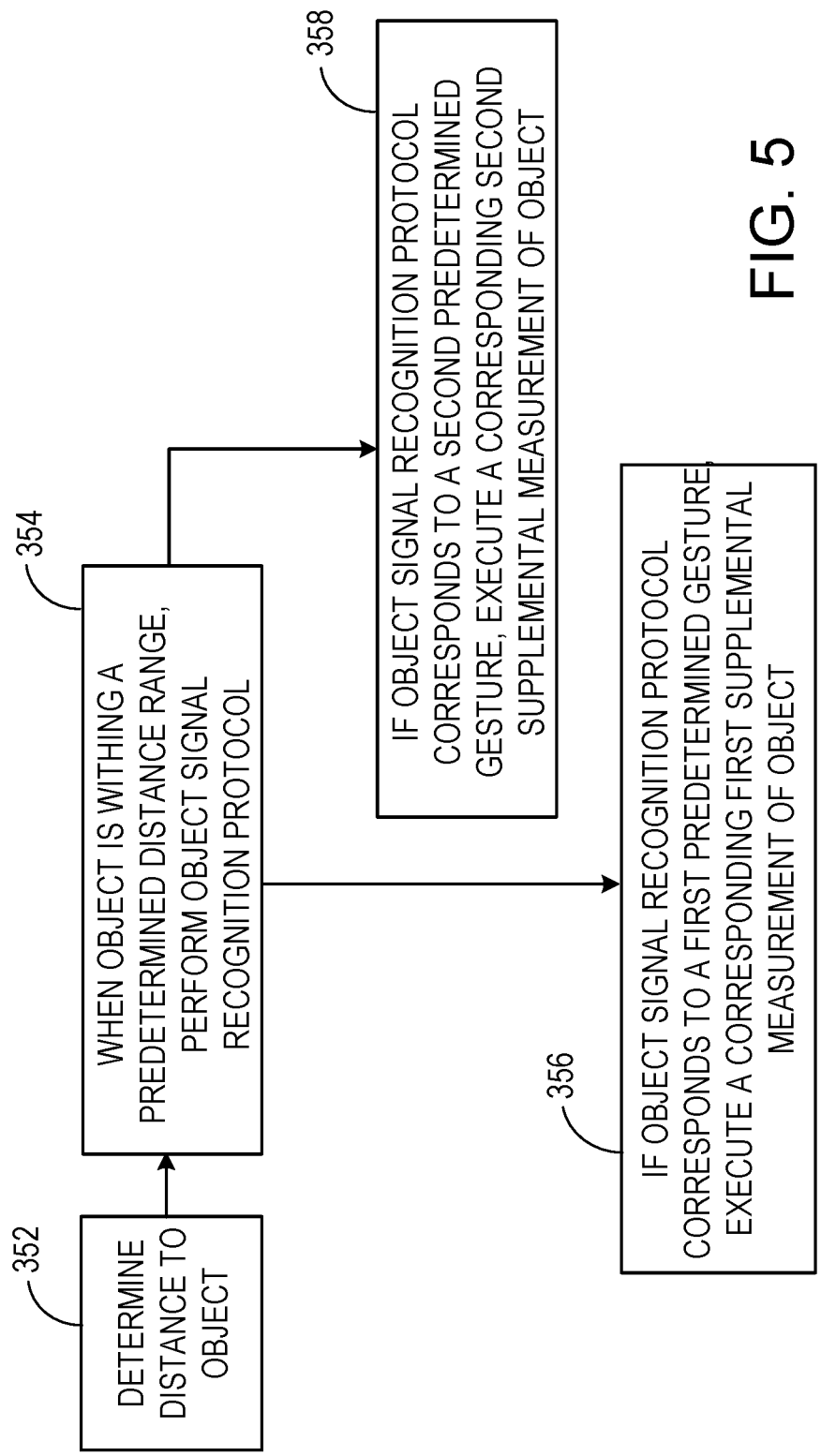
FIG. 5 illustrates an example of a method that includes performance of a supplemental measurement.

Thus, as indicated by FIG. 5, in some instances, the supplemental measurement that is performed by the module or host device depends on the gesture recognized by the object signal-recognition protocol. For example, as indicated by block 352, the distance to an object 140 is determined, e.g., as described above using the module 100 (see, e.g., FIG. 2). When the object 140 is determined to be within a predetermined distance range, the object signal-recognition protocol is executed, as described above (block 354). Then, if the result of the object signal-recognition protocol indicates that the object (or movement of the object) corresponds to a first predetermined gesture, the module or host device executes a first supplemental measurement of the object (block 356). On the other hand, if the result of the object signal-recognition protocol indicates that the object (or movement of the object) corresponds to a different, second predetermined gesture, the module or host device executes a different, second supplemental measurement of the object (block 358).

Figure 6A:
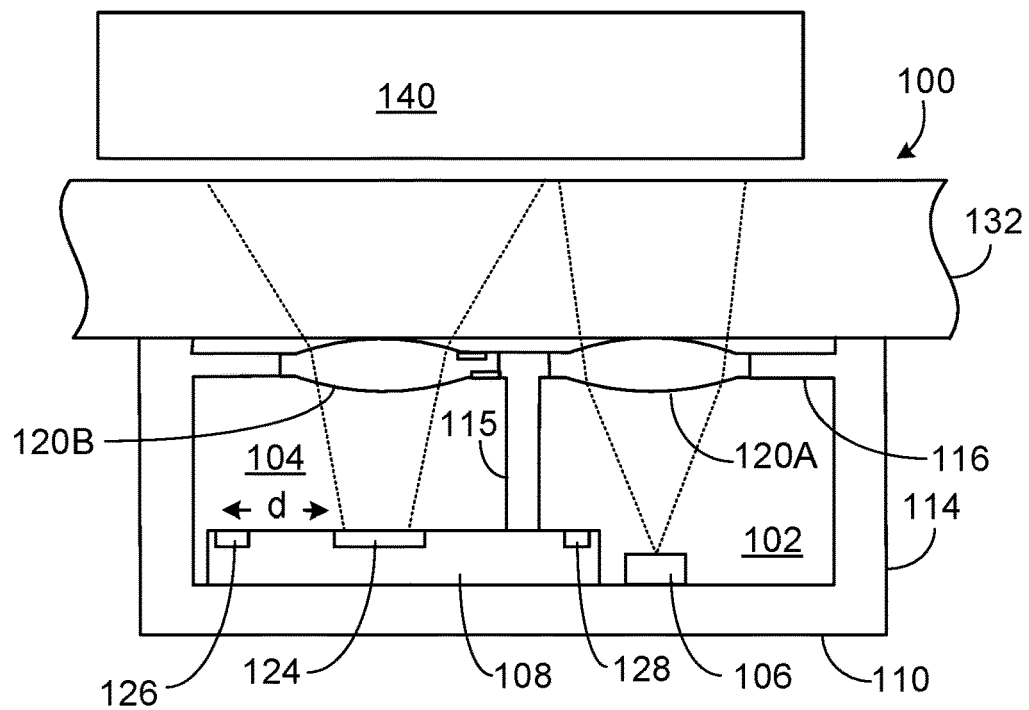
FIG. 6A illustrates an example of an object in close proximity to the cover glass of a host device.
Figure 6B:
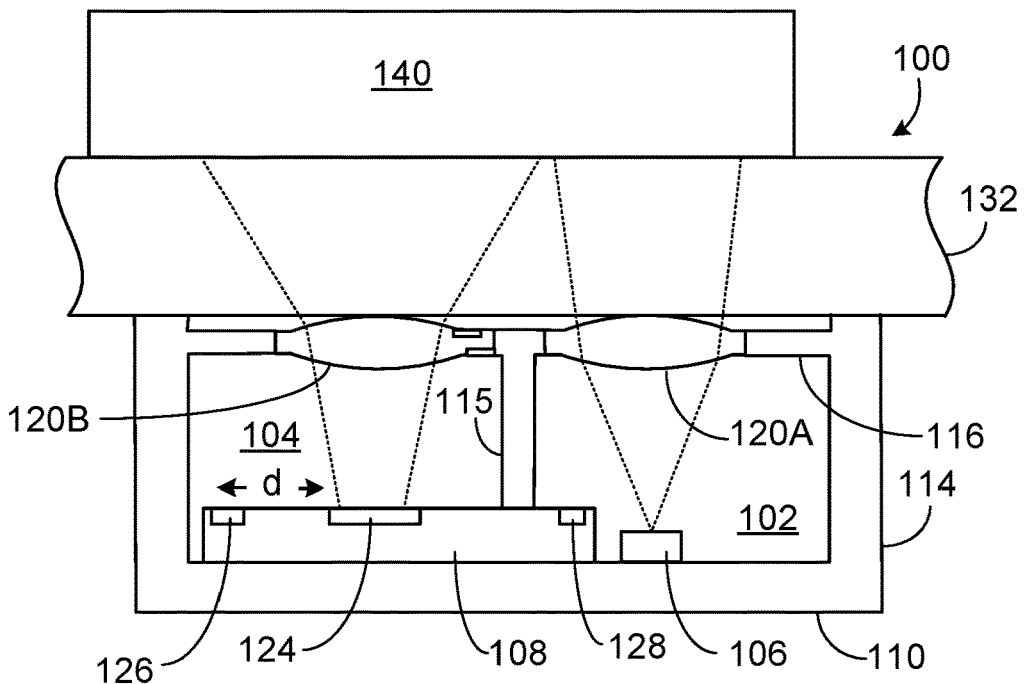
FIG. 6B illustrates an example of an object in contact with the cover glass of a host device.

In some applications, the optoelectronic module 100 is used to determine whether the object 140 is within a particular distance range. The optoelectronic module 100 can determine, for example, the intensity of light incident on the active pixels 124 and/or the spurious-reflection detection pixel 126 reflected from the object 140. The intensity (or amplitude) of the light incident on the active pixels 124 and/or the spurious-reflection detection pixel 126 reflected from the object 140 indicates whether the object 140 is in close proximity to the cover glass (see FIG. 6A) or is in contact with the cover glass of the host device (see FIG. 6B). For example, if the intensity (or amplitude) of the light incident on the active pixels 124 and/or the spurious-reflection detection pixel 126 is below a predetermined threshold intensity (or amplitude) value, then the object 140 can be determined to be close to the cover glass (i.e., within a specified distance from the cover glass, but not in contact with it). On the other hand, if the intensity (or amplitude) of the light incident on the active pixels 124 and/or the spurious-reflection detection pixel 126 is above a predetermined threshold intensity (or amplitude) value, then the object 140 can be determined to be in contact with the cover glass of the host device. The foregoing determinations can be made, for example, by processing circuitry in the host device. Distinguishing between whether the object (a user's finger) is close to the cover glass (but not in contact with it) or in contact with the cover glass can be important for some applications. For example, to determine a user's heart rate, it may be necessary or desirable to ensure that the user's finger or other body part is in contact with the cover glass rather than simply in proximity to it.

FIG. 7 illustrates a method in which an alert protocol can be performed depending whether an object is determined to be within a predetermined distance range (e.g., from the cover glass of the host device). Blocks 402, 404 and 406 correspond, respectively, to blocks 202, 204 and 206 of FIG. 2, described above. Further, as indicated by blocks 408 and 410, distance to the object can be determined as described above based on the light reflected by the object and sensed by the module. If the object distance is determined to be within a predetermined distance range, the intensity of the light incident on the active pixels 124 and/or the spurious-reflection detection pixel 126 is determined (block 412). If the intensity of the light incident on the active pixels 124 and/or the spurious-reflection detection pixel 126 is above a predetermined threshold intensity value, then the object 140 is determined to be in contact with the cover (block 414). In response, a supplemental measurement can be initiated by the module or host device. However, if the intensity of the light incident on the active pixels 124 and/or the spurious-reflection detection pixel 126 is below a predetermined threshold intensity value, then the object 140 is determined not to be in contact with the cover glass (block 416). In response, an alert protocol can be executed (e.g., by the host device). The alert protocol can, for example, alert a user of the host device to bring her finger in contact with the cover glass of the host device.

Various aspects of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus" and "computer" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a smartphone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

A number of implementations have been described. Nevertheless, various modifications may be made without departing from the spirit and scope of the invention. Accordingly, other implementations are within the scope of the claims.

What is claimed is:

1. An apparatus comprising:
    an optoelectronic module comprising:
        a light emitter operable to emit light from the module toward an object outside the module at a first modulation frequency and at a second modulation frequency different from the first modulation frequency; and
        demodulation pixels operable to detect light reflected from the object at the first modulation frequency and at the second modulation frequency; and
    one or more processors collectively operable to:
        subtract out a component in signals detected by the demodulation pixels, wherein the component is caused by a reflection from an element, other than the object, in or on the optoelectronic module or host device in which the optoelectronic module is disposed, so as to determine a phase shift and amplitude resulting from light reflected by the object;
        determine that the object is within a predetermined distance range by determining the distance to the object based at least in part on the phase shift resulting from light reflected by the object;
        execute an object signal-recognition protocol using signals detected by the demodulation pixels; and subsequently initiate execution of a supplemental measurement in response to the object signal-recognition protocol determining that the object satisfies predetermined criteria.

2. The apparatus of claim 1 wherein the one or more processors are operable to execute the object signal-recognition protocol using the distance to the object.

3. The apparatus of claim 1 wherein the one or more processors are operable to execute the object signal-recognition protocol using the amplitude resulting from the light reflected by the object.

4. The apparatus of claim 1 wherein the one or more processors are operable to execute the object signal-recognition protocol using the distance to the object and using the amplitude resulting from the light reflected by the object.

5. The apparatus of claim 1 wherein the one or more processors are operable to use vector manipulation to subtract out the phase shift caused by the reflection from the element in the optoelectronic module or host device in which the optoelectronic module is disposed.

6. The apparatus of claim 5 wherein the reflection is from a smudge on a cover glass of the host device.

7. The apparatus of claim 1 wherein the supplemental measurement includes a measurement of pulse.

8. The apparatus of claim 7 wherein the optoelectronic module is operable to perform the supplemental measurement.

9. The apparatus of claim 1 wherein the one or more processors are operable to determine whether the amplitude resulting from the light reflected by the object is greater than or equal to a predetermined threshold intensity value.

10. The apparatus of claim 9 wherein the one or more processors are operable to initiate execution of the supplemental measurement protocol upon determination that the amplitude resulting from the light reflected by the object is greater than or equal to the predetermined threshold intensity value.

11. The apparatus of claim 1 wherein the one or more processors are operable to determine whether the amplitude resulting from the light reflected by the object is less than a predetermined threshold intensity value.

12. The apparatus of claim 11 wherein the one or more processors are operable to initiate execution of an alert protocol upon determination that the amplitude resulting from light reflected by the object is less than the predetermined threshold intensity value.

13. The apparatus of claim 1 wherein the one or more processors are operable to trigger execution of the supplemental measurement in response to the object signal-recognition protocol recognizing a gesture as a click of a cover glass of a host device in which the module is disposed.

14. The apparatus of claim 1 wherein the one or more processors are operable to trigger execution of the supplemental measurement in response to the object signal-recognition protocol recognizing a gesture as a multi-click of a cover glass of a host device in which the module is disposed.

15. The apparatus of claim 1 wherein the optoelectronic module is operable to execute the supplemental measurement.

16. The module of claim 1 wherein the supplemental measurement is a heart rate measurement.

17. The module of claim 1 wherein the supplemental measurement is a blood oxygen measurement.

* * * * *